United States Patent
Morgan et al.

(10) Patent No.: US 11,553,956 B2
(45) Date of Patent: Jan. 17, 2023

(54) SURGICAL DEVICES WITH VISUAL INDICATORS

(71) Applicant: Ethicon LLC, Guaynabo, PR (US)

(72) Inventors: Nicholas Morgan, Cincinnati, OH (US); Cory Kimball, Cincinnati, OH (US); Christopher Pitaniello, Cincinnati, OH (US); Demetrius Harris, Cincinnati, OH (US); Geoffrey S. Strobl, Williamsburg, OH (US); William D. Shaw, Jr., Cincinnati, OH (US); Ellen Renner, Cincinnati, OH (US); David K. Norvell, Monroe, OH (US)

(73) Assignee: Cilag GmbH International, Zug (CH)

( * ) Notice: Subject to any disclaimer, the term of this patent is extended or adjusted under 35 U.S.C. 154(b) by 273 days.

(21) Appl. No.: 16/375,426

(22) Filed: Apr. 4, 2019

(65) Prior Publication Data
US 2020/0315690 A1    Oct. 8, 2020

(51) Int. Cl.
*A61B 18/14*    (2006.01)
*A61B 18/16*    (2006.01)
*A61B 18/12*    (2006.01)
*A61B 18/00*    (2006.01)

(52) U.S. Cl.
CPC ...... *A61B 18/1445* (2013.01); *A61B 18/1206* (2013.01); *A61B 18/16* (2013.01); *A61B 2018/0063* (2013.01); *A61B 2018/00875* (2013.01); *A61B 2018/126* (2013.01); *A61B 2018/1253* (2013.01); *A61B 2018/1455* (2013.01)

(58) Field of Classification Search
CPC ............... A61B 18/1445; A61B 18/19; A61B 2018/1455; A61B 2018/00875; A61B 2018/0063; A61B 2018/00666
See application file for complete search history.

(56) References Cited

U.S. PATENT DOCUMENTS

| | | | |
|---|---|---|---|
| 7,112,201 B2 | 9/2006 | Truckai et al. | |
| 7,169,145 B2 | 1/2007 | Isaacson et al. | |
| 7,416,101 B2 | 8/2008 | Shelton, IV et al. | |
| 9,675,405 B2 | 6/2017 | Trees et al. | |
| 9,872,738 B2 | 1/2018 | Weir | |
| 10,010,309 B2 | 7/2018 | Bingham | |
| 10,010,366 B2 | 7/2018 | Strobl | |
| 2003/0055417 A1* | 3/2003 | Truckai ............... | A61B 18/1815 606/27 |
| 2007/0173814 A1* | 7/2007 | Hixson ............... | A61B 18/1445 606/51 |

(Continued)

OTHER PUBLICATIONS

U.S. Appl. No. 15/900,096 entitled "Robotic Surgical Instrument Communication" filed Feb. 20, 2018 (32 pages).

(Continued)

*Primary Examiner* — Jaymi E Della
(74) *Attorney, Agent, or Firm* — Mintz Levin Cohn Ferris Glovsky and Popeo, P.C.

(57) ABSTRACT

In general, surgical devices including visual indicators thereon are provided. A user of the device therefore may quickly visually ascertain various operational details of the surgical device and/or various pieces of information about the device and/or tissue of a patient being operated on.

20 Claims, 6 Drawing Sheets

(56) References Cited

U.S. PATENT DOCUMENTS

| | | | |
|---|---|---|---|
| 2008/0249523 A1* | 10/2008 | McPherson | A61B 18/1445 606/41 |
| 2009/0003014 A1* | 1/2009 | Jablonski | A43B 3/0005 362/602 |
| 2010/0198200 A1* | 8/2010 | Horvath | G05G 1/305 606/1 |
| 2012/0116267 A1* | 5/2012 | Kimball | H01M 10/48 606/1 |
| 2013/0253480 A1* | 9/2013 | Kimball | H04L 67/32 606/1 |
| 2014/0104070 A1* | 4/2014 | Plaven | A61B 17/320092 340/815.45 |
| 2017/0135712 A1 | 5/2017 | Boudreaux | |
| 2017/0202608 A1* | 7/2017 | Shelton, IV | A61B 18/1445 |
| 2017/0245854 A1* | 8/2017 | Zemlok | A61B 17/07207 |
| 2019/0046220 A1* | 2/2019 | Chaturvedi | A61B 5/02416 |
| 2019/0059929 A1 | 2/2019 | Shelton, IV et al. | |
| 2020/0038125 A1* | 2/2020 | Farlow | A61B 34/37 |

OTHER PUBLICATIONS

U.S. Appl. No. 15/913,389 entitled "Measuring Impedance For Electrosurgical Tools" filed Mar. 6, 2018 (39 pages).
U.S. Appl. No. 16/115,247 entitled "Determining The State Of An Ultrasonic End Effector" filed Aug. 28, 2018 (282 pages).
U.S. Appl. No. 16/375,338 entitled "Surgical Devices Switchable Between Monopolar Functionality And Bipolar Functionality" filed Apr. 4, 2019 (43 pages).

* cited by examiner

SURGICAL DEVICES WITH VISUAL INDICATORS

FIELD

The present disclosure generally relates to surgical devices with visual indicators thereon to communicate information to a user.

BACKGROUND

Various surgical devices can be used for minimally-invasive surgery to compress, transect, and seal different types of tissue. In general, these devices can have an end effector with a pair of opposed jaws that are configured to engage tissue therebetween and can have a cutting mechanism that is configured to transect tissue engaged by the opposed jaws. The end effector can be configured to apply electrical energy to tissue engaged between the opposed jaws. The application of electrical energy to the engaged tissue can seal and coagulate the tissue, such as to seal tissue being cut by the cutting mechanism to prevent or reduce bleeding.

Various situations can arise during a surgical procedure in which a user wants to have information about the surgical site and/or the surgical device being used. However, the user gathering the information during the surgical procedure can be time consuming, and/or equipment in addition to the surgical device may need to be present to provide the information to the user.

Accordingly, there remains a need for improved information communication about surgical devices to users.

SUMMARY

In general, surgical devices are provided with visual indicators thereon to communicate information to a user about a surgical procedure and/or the surgical device.

In one aspect, an electrosurgical device is provided that in one embodiment includes a housing, an elongate shaft extending from the housing, an end effector operatively connected to a distal end of the elongate shaft, and an electro-luminescent (EL) material. The end effector includes first and second jaws movable between an open position, in which the first and second jaws are spaced apart from one another, and a closed position, in which the first and second jaws cooperate to grasp tissue therebetween. The end effector also includes an electrode configured to conduct radio frequency (RF) energy to tissue in contact therewith. The EL material is configured to provide a light output indicative of a status of the electrosurgical device.

The device can have any number of variations. For example, the EL material can include at least one of an EL wire and an EL tape. In another example, the light output can be configured to be at least one of turned on and off, rhythmically pulse, and illuminate in one or more pre-set colors. In still another example, the electrode can include at least one of a monopolar electrode and a bipolar electrode assembly including an active electrode and a return electrode. In another example, the electrode can include the bipolar electrode assembly and can be configured to conduct the RF energy through tissue grasped between the first and second jaws. In still another example, the electrode can include the monopolar electrode and can be configured to conduct the RF energy through tissue adjacent to the end effector. In still other examples, the electrode can include both the monopolar electrode and the bipolar electrode assembly.

In at least some embodiments, the status of the electrosurgical device can include at least one of an energy modality of the electrosurgical device between monopolar and bipolar modes, if the electrosurgical device is turned on or off, if energy is being presently applied by the electrode to the tissue in contact therewith, an amount of energy being presently applied, if an error occurred during energy application, if the electrode has contacted the tissue, and a type of the tissue that the electrode has contacted.

In at least some embodiments, the electrosurgical device can include a sensor in the end effector configured to measure impedance of the tissue contacted by the electrode. In at least some embodiments, the at least one status can include whether tissue contacted by the electrode has been sealed by energy conducted thereto such that a low measured impedance indicates that the tissue is unsealed and a high measured impedance indicates that the tissue is sealed.

In another example, the material can be configured to receive energy from at least one of the RF energy of the end effector and a sub-therapeutic electrical signal in the electrosurgical device. In yet another example, the electrosurgical device can include an actuator configured to control the EL material. In another example, the EL material can be configured to be controlled by at least one of an amount of RF energy applied to the end effector and a sound in an operating room environment in which the electrosurgical device is used. In still another example, the EL material can include a phosphor material configured to glow when exposed to alternating current of the RF energy.

In another embodiment, an electrosurgical device is provided that includes a housing, an elongate shaft extending from the housing, an end effector coupled to a distal end of the elongate shaft, and an electro-luminescent (EL) light assembly. The end effector is configured to deliver energy to tissue in contact with the end effector. The EL light assembly is positioned at least partially on an external surface of the end effector, and the EL light assembly is configured to display variable real-time information about at least one of an operation of the end effector and a condition of tissue in contact with the end effector.

The device can vary in any number of ways. For example, the EL light assembly can be configured to be at least one of turned on and off, rhythmically pulse, and illuminate in one or more pre-set colors. In another example, the EL light assembly can be electrically connected in parallel with tissue in contact with the end effector such that a brightness of the EL light assembly increases as energy is applied to seal the tissue. In still another example, the EL light assembly can be electrically connected in series with tissue in contact with the end effector such that a brightness of the EL light assembly decreases as energy is applied to the tissue. In yet another example, the EL light assembly can be a light-emitting capacitor.

In another aspect, a surgical method is provided that in one embodiment includes positioning an end effector of an electrosurgical device in contact with tissue while the end effector is coupled to a distal end of an elongate shaft of the surgical device. The method also includes actuating the electrosurgical device to deliver energy to the tissue with an electro-luminescent (EL) light assembly on the electrosurgical device displaying variable real-time information about at least one of an actuation state of the electrosurgical device and a condition of the tissue in contact with the end effector.

The method can vary in any number of ways. For example, actuating the electrosurgical device to deliver energy to the tissue can include delivering energy to seal the tissue until the EL light assembly indicates that the tissue is sealed. In at least some embodiments, the EL light assembly indicating the tissue is sealed can further include the end effector measuring impedance of the tissue such that a low measured impedance indicates that the tissue is unsealed and a high measured impedance indicates that the tissue is sealed.

In still another example, the method can further include switching the electrosurgical device between a monopolar mode and a bipolar mode such that the EL light assembly indicates which mode is currently selected.

BRIEF DESCRIPTION OF DRAWINGS

This invention will be more fully understood from the following detailed description taken in conjunction with the accompanying drawings, in which.

DETAILED DESCRIPTION

Figure 1:
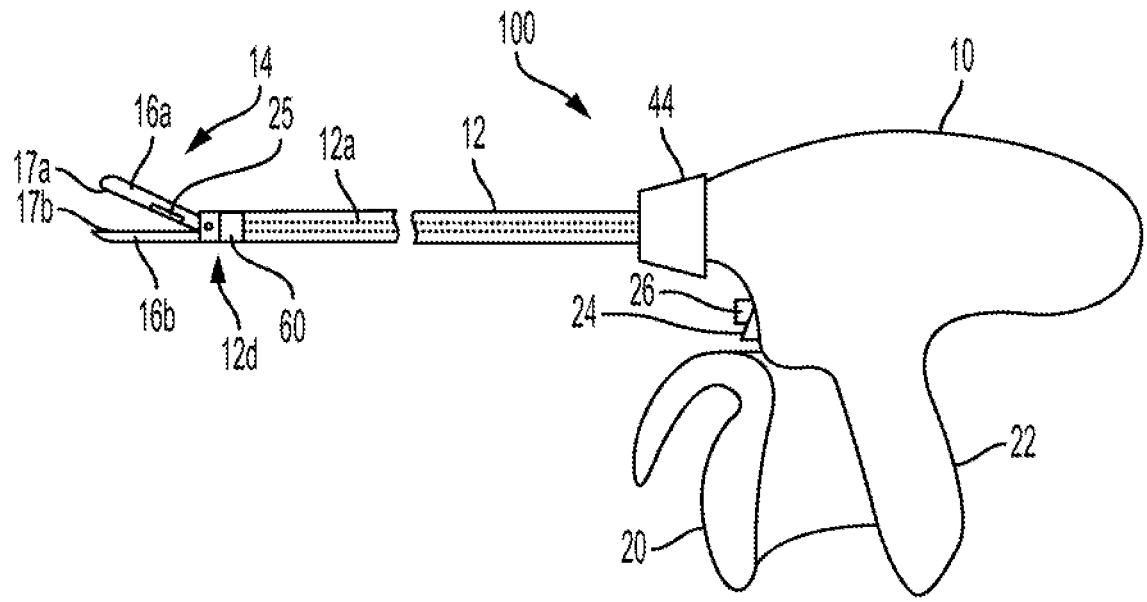
FIG. 1 is a side schematic view of one embodiment of a surgical device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment, each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, surgical devices including visual indicators thereon are provided. In an exemplary embodiment, a surgical device is configured to have an electro-luminescent (EL) indicator thereon to provide visual indication of a status, such as a status of the device itself or a status of tissue with which the device is interacting. A user of the device therefore may quickly visually ascertain various operational details of the surgical device and/or various pieces of information about the device and/or tissue of a patient being operated on. For example, when a user believes an action is being performed by the device, such as the device powering on, sealing energy being applied by the device to tissue, contacting tissue, etc., the visual indicator can communicate information to the user to indicate a status of such an action. A user can thus operate the surgical device with greater certainty and without having to speculate or remember certain information about the device and/or the surgical procedure while also focusing on safely operating on a patient, which may increase safety and efficiency of the surgical procedure and/or reduce overall costs.

An EL indicator may be easily incorporated into a surgical device. An electrosurgical device uses power source(s) and/or generator(s) that provide high voltage and alternating current when treating tissue, and the EL indicator can use the same high voltage and alternating current as the surgical device to illuminate. As such, material of the EL indicator can operate effectively with power source(s) and/or generator(s) used with the surgical device for another purpose (e.g., energy application to tissue), which may facilitate incorporation of the EL indicator into existing surgical devices and/or into designs of new surgical devices.

FIGS. 1-7 illustrate one embodiment of a surgical device 100. The illustrated surgical device 100 includes a housing 10, an elongate shaft 12, and an end effector 14 configured to grasp tissue. The housing 10 can be any type of pistol-grip, scissor grip, pencil-grip, or other type of handle known in the art that is configured to carry various actuators, such as actuator levers, knobs, triggers, sliders, etc. for actuating various functions such as rotating, articulating, approximating, and/or firing the end effector 14. In the illustrated embodiment, the housing 10 is coupled to a stationary grip handle 22 and a closure grip handle 20 configured to move relative to the stationary grip handle 22 to open and close the end effector 14. The shaft 12 extends distally from the housing 10 and includes at least one lumen 12a extending therethrough for carrying mechanisms for actuating the end effector 14.

The end effector 14 can have a variety of sizes, shapes, and configurations. As shown in FIG. 1, the end effector 14 includes a first, upper jaw 16a and a second, lower jaw 16b disposed at a distal end 12d of the shaft 12. The jaws 16a, 16b are configured to move between an open position, in which the jaws 16a, 16b are spaced a distance apart, and a clamping or closed position, in which the jaws 16a, 16b are moved toward one another and are substantially opposed. The jaws 16a, 16b in the closed position are configured to engage tissue therebetween and apply a force to tissue disposed therebetween. In the illustrated embodiment, the end effector 14 is configured to move between the open and closed positions by the upper jaw 16a pivoting relative to the shaft 12 and relative to the lower jaw 16b while the lower jaw 16b remains stationary. In other embodiments, both jaws 16a, 16b can be movable to move the end effector 14 between the open and closed positions, or the lower jaw 16b can be configured to pivot relative to the shaft 12 and the upper jaw 16a to move the end effector 14 between the open and closed positions. The jaws 16a, 16b have a substantially elongate and straight shape, however one or both of the jaws 16a, 16b can curve in various directions, such as being curved along a longitudinal length thereof. The jaws 16a, 16b can have any suitable axial length for engaging tissue, and the length can be selected based on the targeted anatomical structure for transection and/or sealing.

Figure 2:
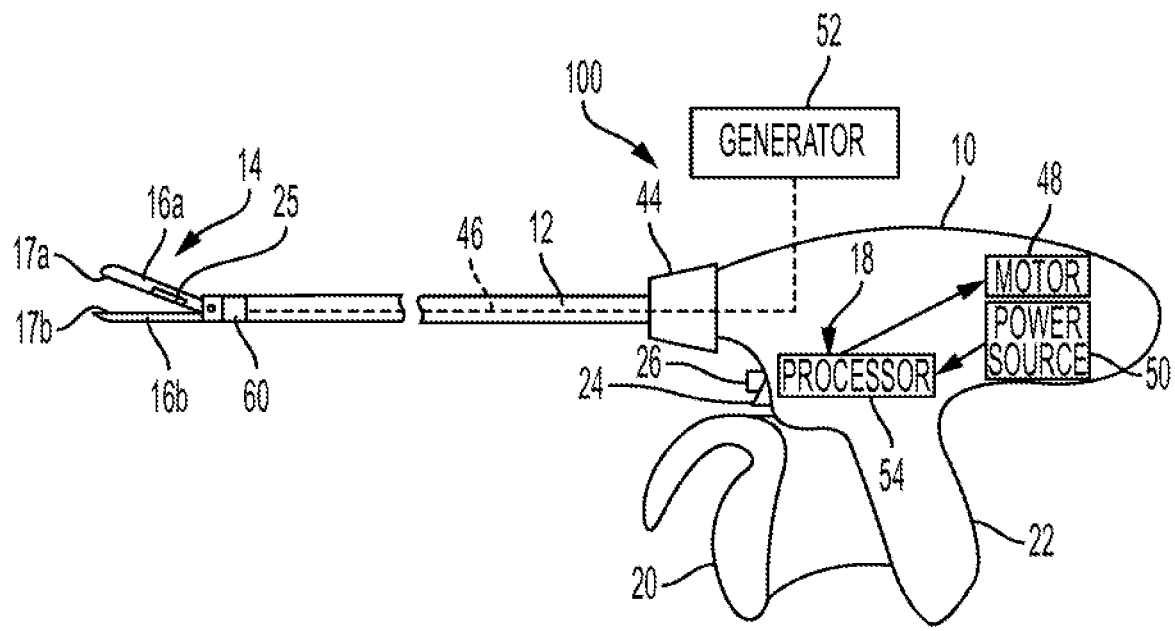
FIG. 2 is a side, partially transparent view of the surgical device of FIG. 1 operatively coupled to a generator.
Figure 4:
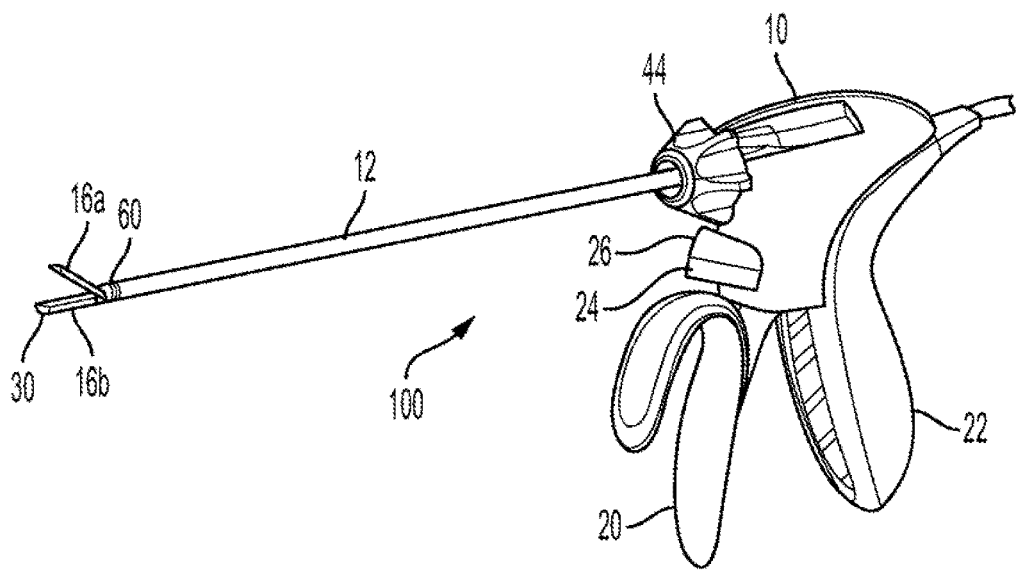
FIG. 4 is a perspective view of the surgical device of FIG. 1.
Figure 5:
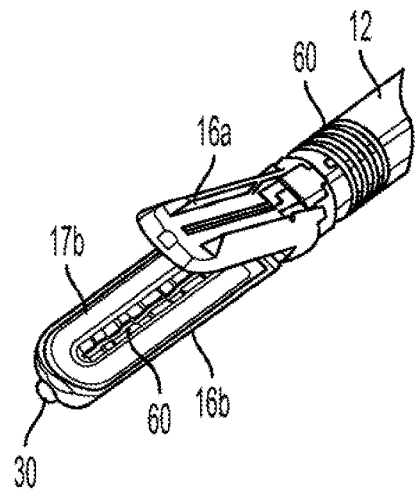
FIG. 5 is a perspective view of a distal portion of the surgical device of FIG. 1.

The closure handle 20 is configured to pivot relative to and toward and away from the stationary handle 22 to move the end effector 14 between the open and closed positions. In particular, the closure handle 20 is movable between a first position and a second position. In the first position, which is illustrated in FIGS. 1, 2, and 4, the closure handle 20 is offset and spaced apart from the stationary handle 22, and the jaws 16a, 16b of the end effector 14 are open, as shown in FIGS. 1, 2, and 4-7. In at least some embodiments the closure handle 20 is biased to the first position such that the end effector 14 is biased to be open. In the second position, the closure handle 20 is positioned adjacent to, or substantially in contact with, the stationary handle 22, and the jaws 16a, 16b of the end effector 14 are closed. Further description of embodiments of end effector opening and closing is provided in U.S. Pat. No. 10,010,309 entitled "Surgical Device With Overload Mechanism" filed Oct. 10, 2014, which is hereby incorporated by reference in its entirety.

In at least some embodiments the device 100 includes a locking feature configured to lock the closure handle 20 in position relative to the stationary handle 22, as will be appreciated by a person skilled in the art. For example, the locking feature can be configured to automatically engage when the closure handle 20 is moved to the second position, e.g., is positioned adjacent to, or substantially in contact with, the stationary handle 22. For another example, the locking feature can be configured to automatically engage at each of a plurality of positions the closure handle 20 is pivoted through between the first and second positions, such as via ratcheting.

The closure handle 20 can use manual or powered components. In manual embodiments the closure handle 20 is configured to be manually moved (e.g., by a user directly or by a user indirectly via robotic surgical control) to manually open/close the end effector 14 using various components, e.g., gear(s), rack(s), drive screw(s), drive nut(s), etc. disposed within the housing 10 and/or shaft 12.

In powered embodiments, the closure handle 20 is configured to be manually moved (e.g., by a user directly or by a user indirectly via robotic surgical control), thereby causing the end effector 14 to open/close either fully electronically or electronically in addition to manual power. In this illustrated embodiment, as shown in FIG. 2, the device 100 is powered and includes a motor 48, a power source 50, and a processor 54, which in this illustrated embodiment are each disposed in the housing 10. Manual movement of the closure handle 20 is configured to cause the processor 54 to transmit a control signal to the motor 48, which is configured to interact with various components of the device 100 to cause the jaws 16a, 16b to open/close. The power source 50 is configured to provide on-board power to the processor 54 and the motor 48. In other embodiments, the processor 54 and/or the motor 48 can be configured to be powered instead, or additionally, with an external power source.

The device 100 can include one or more sensors to facilitate powered end effector opening and closing and/or other device features, such as tissue cutting or impedance measurement. For example, one or more sensors 25 can be placed in or adjacent to the end effector 14 to sense a parameter related to the device 100 and to communicate the sensed data to the processor 54 and/or an external device either through wires in the device 100 or wirelessly. Examples of parameters that the sensor 25 can be configured to sense include use status of the device 100, force or torque, pressure, type of staple cartridge seated in the end effector 14 (when the device 100 is a stapler), presence of a staple cartridge within the end effector 14 (when the device 100 is a stapler), impedance of tissue grasped by the jaws 16a, 16b, an amount of tissue grasped by the jaws 16a, 16b, position of a cutting element relative to the end effector 14, angle of the jaws 16a, 16b, movement of the closure handle 20, rotation of the shaft 12, actuation of actuators 24, 26 and/or an electrical mode of the device (discussed further below), etc. The end effector 14 can have a single sensor or can have multiple sensors, in which case each of the multiple sensors can be configured to sense a different parameter. The illustrated sensor 25 is shown at the end effector 14, but various sensors can be incorporated into any one or more of the end effector 14, the shaft 12, and the housing of the device 100, such as position sensors, force sensors, torque sensors, etc., to provide data regarding various operational aspects of the device 100. Various embodiments of exemplary sensors are further described in U.S. patent application Ser. No. 15/900,096 entitled "Robotic Surgical Instrument Communication" filed Feb. 20, 2018, U.S. patent application Ser. No. 15/913,389 entitled "Measuring Impedance For Electrosurgical Tools" filed Mar. 6, 2018, U.S. Patent Pub. No. 2019/0059929 entitled "Methods, Systems, And Devices For Controlling Electrosurgical Tools" filed Aug. 29, 2017, U.S. Pat. No. 7,416,101 entitled "Motor-Driven Surgical Cutting And Fastening Instrument With Loading Force Feedback" filed Jan. 31, 2006, and U.S. Pat. No. 9,675,405 entitled "Methods And Devices For Controlling Motorized Surgical Devices" filed Apr. 8, 2014, which are hereby incorporated by reference in their entireties.

Figure 3:
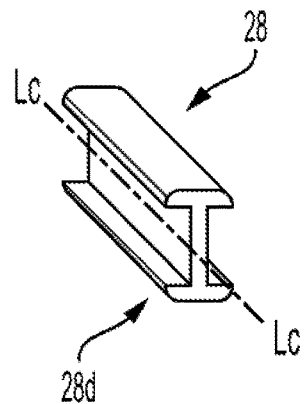
FIG. 3 is a perspective view of a compression member of the surgical device of FIG. 1.

The surgical device 100 includes a cutting or firing actuator 24 configured to be actuated to advance a cutting element to cut tissue grasped between the jaws 16a, 16b. While the actuator 24 can have various configurations, e.g., buttons, knobs, triggers, etc., the illustrated actuator 24 is a button configured to be depressed. The cutting actuator 24 can be in mechanical or electrical communication with various gear(s), rack(s), drive screw(s), drive nut(s), motor(s) (e.g., the motor 48), and/or processor(s) (e.g., the processor 54) to cause the cutting element's movement when the cutting actuator 24 is actuated. The cutting element is configured to transect tissue captured between the jaws 16a, 16b and can be sized and shaped to transect or cut various thicknesses and types of tissue. In one exemplary embodiment, as shown in FIG. 3, an I-beam compression member 28 is configured to travel along a longitudinal axis Lc through slots formed in each jaw 16a, 16b to pull the jaws into a parallel orientation, to compress tissue therebetween, and to transect tissue using a cutting element on the distal end 28d thereof, such as by the distal end 28d having a sharp cutting edge or having a knife blade mounted thereon.

The surgical device 100 includes a sealing actuator 26 configured to be actuated to cause energy, such as radiofrequency (RF) or ultrasound energy, to be applied to tissue engaged by the end effector 14. For example, when RF energy is applied to the device, alternating current (AC) can pass through the device 100 and engaged or contacted tissue. While the actuator 26 can have various configurations, e.g., buttons, knobs, triggers, etc., the illustrated actuator 26 is a button configured to be depressed. In other embodiments, instead of including a cutting actuator 24 and a sealing actuator 26, a surgical device can include a combined cutting and sealing actuator configured to be actuated to simultaneously cause cutting and sealing.

The device 100 includes various components configured to facilitate the delivering of energy to tissue. These components can be disposed at various locations in the device 100, such as in the housing 10, the shaft 12, and/or in one or both of the jaws 16a, 16b. Actuating the sealing actuator 26 is configured to cause a signal to be transmitted to the processor 54, which in response is configured to cause delivery of energy from a generator 52 and/or the power source 50 to tissue engaged by the end effector 14. The generator 52 can be incorporated into the handle portion 10 or, as in this illustrated embodiment as shown in FIG. 2, can be a separate unit that is configured to be electrically connected to the surgical device 100. The generator 52 is any suitable generator known in the art, such as an RF generator or an ultrasound generator.

The lumen 12a of the shaft 12 has disposed therein one or more electrical paths 46, e.g., leads, conductive members, wires, etc., configured to deliver electrical energy to the end effector 14 in response to actuation of the sealing actuator 26. The one or more electrical paths 46 are operatively coupled to the generator 52 in this illustrated embodiment, with the generator 52 being configured to supply energy to the one or more electrical paths 46. Upon actuation of energy delivery, energy is configured to be delivered to one or more electrodes in one or both of the jaws 16a, 16b via the one or more electrical paths 46 for delivering electrical current to tissue grasped therebetween to effect sealing, marking, cutting, etc. of the tissue. Further description of embodiments of energy application by surgical devices is provided in U.S. Pat. No. 10,010,366 entitled "Surgical Devices And Methods For Tissue Cutting And Sealing" filed Dec. 17, 2014, U.S. Pat. No. 7,169,145 entitled "Tuned Return Electrode With Matching Inductor" filed Nov. 21, 2003, U.S. Pat. No. 7,112,201 entitled "Electrosurgical Instrument And Method Of Use" filed Jan. 22, 2003, and U.S. Patent Pub. No. 2017/0135712 entitled "Methods And Devices For Auto Return Of Articulated End Effectors" filed Nov. 17, 2015, which are hereby incorporated by reference in their entireties.

The device 100 has bipolar functionality in which energy applied to tissue engaged by the end effector 14 is bipolar energy applied by a delivery or active electrode 17a and received by a return electrode 17b. One of the jaws 16a, 16b (the upper jaw 16a in this illustrated embodiment) includes the active electrode 17a on a tissue-facing surface thereof, and the other one of the jaws 16a, 16b (the lower jaw 16b in this illustrated embodiment) includes the return electrode 17b on a tissue-facing surface thereof. The return electrode 17b is electrically isolated from the active electrode 17a such that energy can be applied to tissue grasped between the jaws 16a, 16b from the active electrode 17a and have a return path through the return electrode 17b. The bipolar energy is thus configured to be delivered to tissue grasped between the jaw 16a, 16b when the end effector 14 is in the closed position.

The device 100 also has monopolar functionality in which energy applied to tissue engaged by the end effector 14 is monopolar energy applied by a monopolar electrode 30 in the form of a conductive shaft, as illustrated in FIGS. 4-7 (the monopolar electrode 30 is obscured in FIGS. 1 and 2). An energy return path can be through surrounding tissue, the device 100 generally, a ground pad placed on a patient's body, a separate electrical return line or path, a return electrode, etc. While tissue and/or vessel sealing can be accomplished by applying bipolar energy to tissue grasped by the end effector 14 (e.g., located and clamped between the jaws 16a, 16b), it can be beneficial to apply spot energy to target tissue or a vessel that is adjacent to the end effector 14 and not grasped thereby (e.g., located outside of the jaws 16a, 16b) to allow for spot coagulation, non-clamping sealing and/or hemostasis, marking tissue, cutting or searing tissue, etc. The device's monopolar functionality allows for this spot energy application. The device 100 thus includes mechanisms for advancing and retracting the monopolar electrode 30 for applying the spot energy. When advanced, at least part of the monopolar electrode 30 protrudes from the end effector 14 to deliver energy to tissue, and when retracted, the monopolar electrode 30 is at least partially withdrawn into the end effector 14 such that at least a portion of the monopolar electrode 30 is protected by the end effector 14.

A surgeon or other medical professional may want to apply each of bipolar energy and monopolar energy during the course of performing a surgical procedure. Bipolar energy can be useful for focused energy application to tissue since the energy is applied to the grasped tissue. Monopolar energy is not as focused since the tissue may serve as the return pole and since the energy is not being applied to tissue located between and being pressed by the end effector's jaws 16a, 16b. Monopolar energy is still useful, however, such as for cutting tissue that the user does not want to bleed, as monopolar energy is configured to be hot enough to provide for coagulation. The device 100 is configured to selectively apply each of bipolar energy and monopolar energy such that devices do not need to be switched out during performance of a surgical procedure since the same device 100 can apply each of bipolar energy and monopolar energy any number of times as desired by a surgeon or other medical professional. However, surgical devices that are configured to apply only one of bipolar energy or monopolar energy can also incorporate the visual indicators discussed herein.

The device 100 includes a switching mechanism configured to switch the device 100 between a bipolar mode, in which bipolar energy is applied via the bipolar electrodes 17a, 17b in response to actuation of the sealing actuator 26, and a monopolar mode, in which monopolar energy is applied via the monopolar electrode 30 in response to actuation of the sealing actuator 26. Energy application may thus be achieved via a same actuation mechanism (the sealing actuator 26) regardless of whether the type of energy to be applied is bipolar or monopolar. However, in other embodiments, more than one actuation mechanism can be provided on the device 100 for dedicated actuation of either bipolar electrodes 17a, 17b or monopolar electrode 30 such that a switching mechanism is unnecessary.

The switching mechanism can have a variety of configurations. For example, the switching mechanism in the illustrated embodiment includes a movable knob 44 that is configured to move between first and second positions to move the surgical device 100 between monopolar and bipolar modes. The knob 44 can be configured to translate longitudinally, e.g., slide linearly, relative to the housing 10 to move between the first and second positions. Longitudinal movement of the knob 44 can also be configured to cause selective advancement and retraction of the monopolar electrode 30 of the device 100. The knob 44 is also configured to be rotated relative to the housing 10 to cause the shaft 12 and the end effector 14 to rotate about a longitudinal axis of the shaft 12. However, a variety of other switching mechanisms are possible, such as buttons, switches, etc. on the housing 10. Embodiments of changing between monopolar and bipolar modes of a surgical device are further described in U.S. patent application Ser. No. 16/375,338 entitled "Surgical Devices Switchable Between Monopolar Functionality And Bipolar Functionality" filed on Apr. 4, 2019, which is incorporated by reference herein in its entirety.

The device 100 includes a mode sensor 18 configured to recognize whether the device 100 is in the bipolar mode or monopolar mode. The mode sensor 18 can have any of a variety of configurations, such as pressure sensor(s) or locations sensor(s) configured to monitor the switching mechanism; various buttons, switches, etc. on the housing 10 that can be incorporated into the switching mechanism; etc. The mode sensor 18 is operatively coupled to the processor 54 and is configured to provide a signal thereto indicative of its monitored parameter(s). The processor 54 is configured to direct energy, e.g., from the generator 52, to the active electrode 17a (for bipolar energy) or the monopolar electrode 30 (for monopolar energy) based on the sensed mode.

As illustrated in FIGS. 1-7, the device 100 includes at least one visual indicator 60 disposed thereon. The visual indicator 60 is configured to provide a light output visible to a user that is indicative of a status of the device 100, such as a real-time operational condition of the device 100 or information about tissue contacting the end effector 14. The status of the device 100 indicated by the indicator 60 can be a variety of different information, such as an energy modality of the device 100 between the monopolar and bipolar modes, if the device 100 is turned on or off, if energy is being presently applied by the end effector 14 to tissue in contact therewith, an amount of energy being presently applied, if an error is occurring or has occurred during energy application, if tissue and/or a vessel has been almost or is entirely sealed, if the end effector 14 has contacted tissue, a type of tissue that has been contacted, a position of the device 100 in the patient, a position of the cutting element in the end effector 14, if captured tissue has been transected, etc. The light output of the visual indicator 60 can be configured to convey information in a variety of ways, such as by being turned on and off, rhythmically pulsing in one or more light patterns, illuminating in one or more pre-set colors (such as red, blue, green, orange, yellow, etc.), altering a brightness or intensity of the light output, some combination of these, etc. In at least some embodiments, the light output of the indicator 60 can be used as lighting for the surgical site. The device 100 can be configured to convey more than one piece of information, such as through using more than one indicator 60 and/or through a single indicator 60 that is configured to illuminate differently in different scenarios.

As illustrated, the visual indicator 60 is wrapped around a distal portion of the shaft 12 and extends along a portion of the lower jaw 16b. However, the indicator 60 can be disposed at one or more additional or alternate areas on the device 100, such as along the upper jaw 17a, at a proximal portion and/or an intermediate portion of the shaft 12, at the housing 10, along various device elements, etc., depending on factors such as the information desired to be conveyed to a user, a size of the device, etc.

The visual indicator 60 is configured to receive energy therethrough to cause the indicator 60 to illuminate. In the illustrated embodiment, the visual indicator 60 is in electrical communication, through the one or more electrical paths 46, with one or more of the power source 50 and the generator 52, as discussed further below. The indicator 60 can also be in communication with the processor 54 in at least some embodiments to receive illumination instructions therefrom, as discussed further below.

In an exemplary embodiment, the visual indicator 60 includes an electro-luminescent (EL) material configured to generate light when energy is applied thereto. The illustrated visual indicator 60 is an EL wire, however other configurations using EL material are possible, such as tapes, spots, etc. The EL wire is a single EL wire wrapped around the shaft 12 and extending into the lower jaw 16b in this illustrated embodiment, but multiple EL wires can be used. An exemplary EL material includes a first conductor coated in a phosphor and a second conductor. When energy is applied to the first and second conductors, the phosphor is configured to glow in a range of pre-selected colors, such as red, blue, green, orange, yellow, etc., for example by using various coatings on the material that cause a certain color to be seen, as will be appreciated by a person skilled in the art. In at least some embodiments, the indicator 60 includes at least two EL materials each configured to glow in a different color. Providing light capability in two or more different colors may allow different colors to indicate different statuses. The phosphor can be composed of any of a variety of different materials, such as oxides, nitrides, silicon, an activator such as copper or silver, etc.

In at least some embodiments, the indicator 60 can be a thin layer that is sprayed or painted onto one or more surfaces of the device 100. For example, a phosphor can be sprayed or painted onto a surface of the device 100 to provide a thin coating that will not interfere with device functions while still acting as a visual indicator as described herein. Because phosphor can be provided in such minimal space, phosphor for the indicator 60 can be easily sprayed or coated along various device elements without having to substantially alter external or internal structures or geometries of the surgical device 100. For example, phosphor can be sprayed or painted onto a cutting element configured to translate along the end effector 614, thereby allowing the indicator 60 to inform a user a location of the cutting element, actuation of the firing trigger 24, whether transection of tissue grasped by the end effector 14 has been performed, etc.

In at least some embodiments, the EL material can be encapsulated in a variety of different transparent materials to provide protection for the EL material, such as polyethylene terephthalates (PET, PETG), polycarbonates (PC), etc. The transparent material can be applied, for example, similar to a heat shrink.

Figure 6:
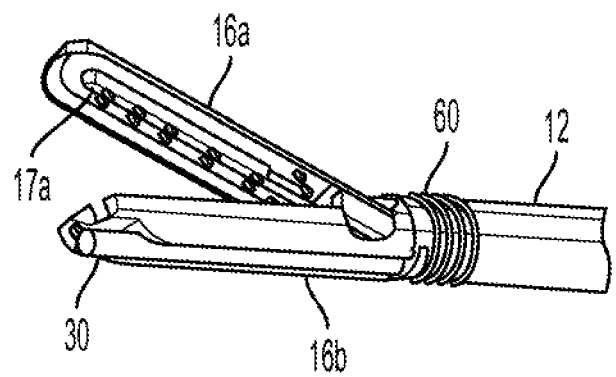
FIG. 6 is another perspective view of a distal portion of the surgical device of FIG. 1.
Figure 6A:
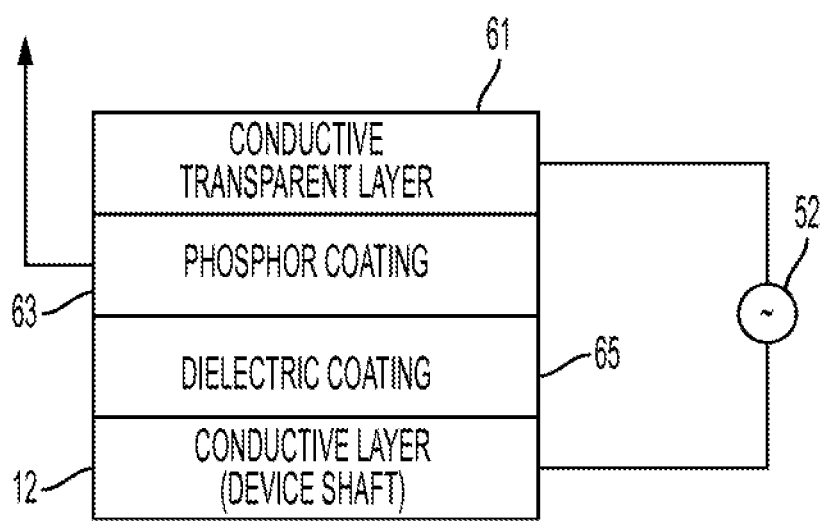
FIG. 6A is a schematic diagram illustrating one embodiment of a portion of the device of FIG. 1.

FIG. 6A illustrates one embodiment of the indicator 60 including three layers 61, 63, 65 disposed on a conductive layer. In this illustrated embodiment the conductive layer is the metal shaft 12 or a layer thereon. In other embodiments the conductive layer can be another conductive component of the device 100 on which the indicator 60 is disposed. The conductive layer can be any of a variety of conductive materials, such as PEDOT:PSS (poly(3,4-ethylenedioxythiophene) polystyrene sulfonate), silver nano-wires, an electrically conductive thin film, etc. The indicator 60 includes a dielectric coating 65 (e.g., barium nitrate or other dielectric) disposed on the shaft 12, a phosphor coating 63 disposed on the dielectric coating 65, and a conductive transparent layer 61 disposed on the phosphor coating 63. Light emits from the phosphor coating layer 63, as shown by the arrow pointing away from the phosphor coating layer 63. FIG. 6A also illustrates the generator 52 operatively coupled to the indicator 60, although as discussed further below various power and connection configurations are possible.

Figure 7:
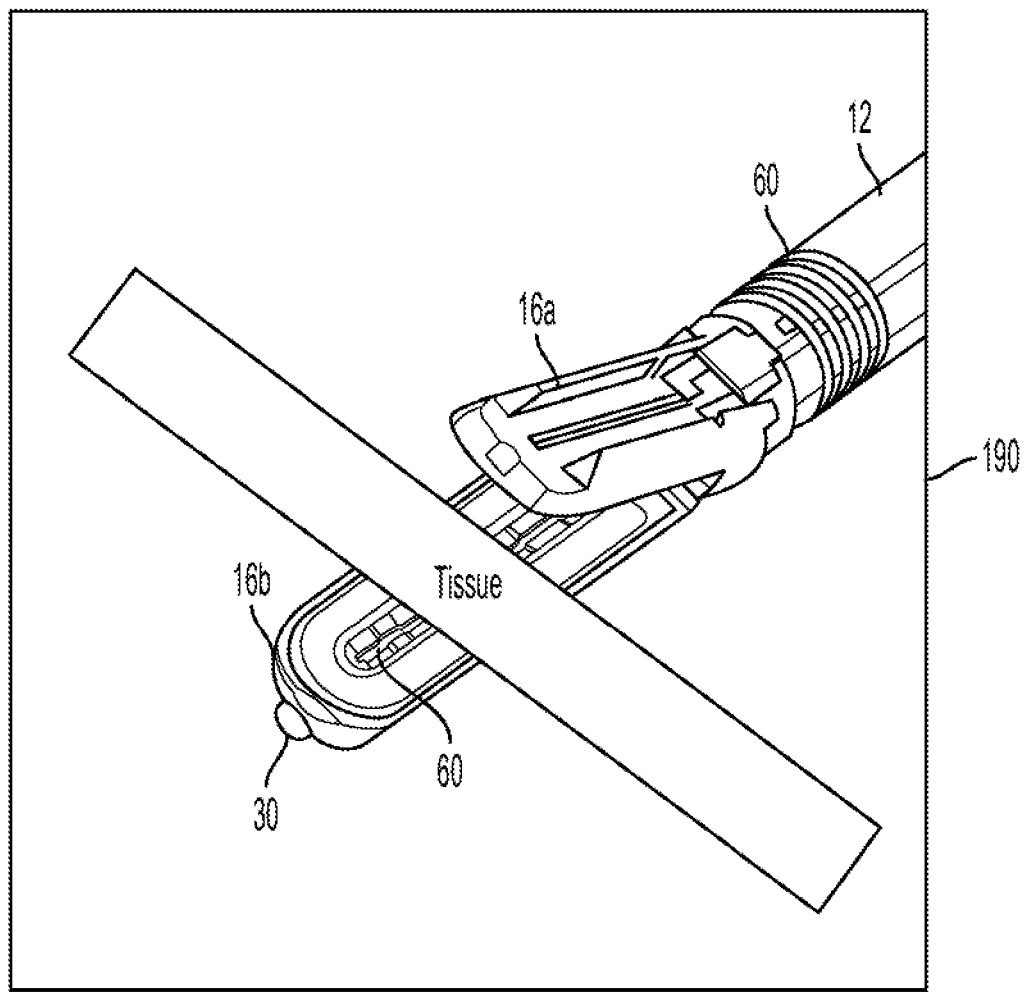
FIG. 7 is a view of one embodiment of a display showing a distal portion of the surgical device of FIG. 1.

The indicator 60 can be directly visualized by a user, or the indicator 60 can be indirectly visualized by a user by seeing the indicator 60 on a display screen showing the device 100 in use during a surgical procedure. One or both of direct and indirect visualization may occur during the course of a surgical procedure. FIG. 7 illustrates one embodiment of a display screen 190 showing the device 100, including the indicator 60, thereon. For example, during laparoscopic surgery, a user can view the visual indicator 60 on a laparoscopic scope video feed shown on the screen 190. In at least some embodiments, the screen 190 can be a part of a robotic surgical system. Further description of embodiments of displays is provided in U.S. Pat. No. 9,872,738 entitled "Methods, Systems, And Devices For Control Of Surgical Tools In A Robotic Surgical System" filed Jan. 6, 2016, which is hereby incorporated by reference in its entirety.

A variety of different electrical configurations for the visual indicator 60 and the device 100 can be used depending on the desired information to be conveyed to the user by the indicator 60. The visual indicator 60 can be configured to be in electrical communication with the bipolar electrodes 17a, 17b and vary illumination as the electrodes 17a, 17b interact with tissue of a patient, in electrical communication with the monopolar electrode 30 and vary illumination as the electrode 30 interacts with tissue, and/or in electrical communication with the processor 54 and vary illumination based on data from one or more sensors in the device 100. The electrical configurations discussed below are not mutually exclusive, and a single surgical device 100 can incorporate one or more of the electrical configurations depending on the desired information to be conveyed and how many visual indicators are used in the device 100. Which electrical configuration(s) are used will thus be determined based on desired information to be conveyed to a user.

When the visual indicator 60 is in electrical communication with the bipolar electrodes 17a, 17b or the monopolar electrode 30, the visual indicator 60 can either receive current from the generator 52 upon application of energy from the generator 52 to the electrode (active electrode 17a or monopolar electrode 30), resulting in passive indication, or receive current from the power source 50 and/or the generator 52 independently of when energy is being applied to the electrode (active electrode 17a or monopolar electrode 30) from the generator 52, resulting in active indication. When the indicator 60 varies illumination based on data from one or more sensors in the device 100, the indicator 60 receives current from the power source 50 and/or the generator 52 independently of when energy is being applied, resulting in active indication. Passive indication can be used to directly reflect energy being applied by the generator 52 to electrodes 17a, 30, while active indication can be used to reflect a variety of information, as discussed further below.

FIGS. 8-13 illustrate various exemplary embodiments of electrical pathways that can be used in the device 100 to facilitate selective lighting of the indicator 60 when the indicator 60 is in electrical communication with the bipolar electrodes 17a, 17b or with the monopolar electrode 30. The indicator 60 in these embodiments is thus configured to illuminate as energy is being applied.

Figure 8:
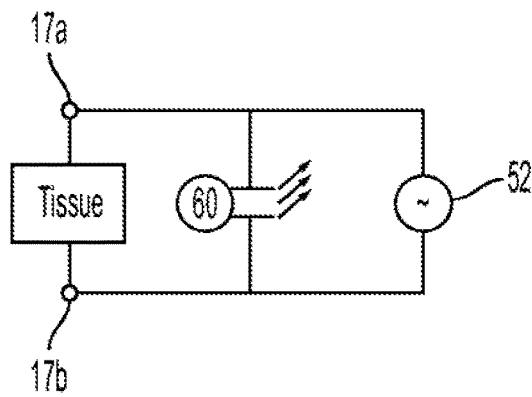
FIG. 8 is an electrical diagram of another embodiment of an electrical pathway for the surgical device of FIG. 1.

FIG. 8 illustrates one embodiment of a bipolar electrical configuration of the device 100 in which the indicator 60 is passively connected to the generator 52, meaning that the indicator 60 will receive current and provide illumination for indication only when the device 100 is in bipolar mode and during application of energy from the generator 52 using the electrodes 17a, 17b in contact with tissue. While the indicator 60 in such a configuration relies on application of energy to the electrodes 17a, 17b to provide indication, a level of illumination of the indicator 60 is directly influenced by an amount of energy being provided by the generator 52 to the electrodes 17a, 17b. As such, illumination of the visual indicator 60 directly reflects and indicates energy being supplied by the generator 52 to the active electrode 17a (and thus indicates when energy is being applied by the electrodes 17a, 17b to grasped tissue) and directly reflects and indicates an amount of energy being applied because illumination will increase with an increase in the amount of energy applied to tissue, and whether or not tissue and/or a vessel gripped by the jaws 16a, 16b has been almost or is entirely sealed based on illumination levels caused by changes in tissue impedance.

In FIG. 8, the visual indicator 60, the generator 52 in electrical communication with the electrical path 46, and tissue grasped between the bipolar electrodes 17a, 17b are electrically connected in parallel with each other. Thus, when tissue is grasped between the electrodes 17a, 17b, an electrical circuit is completed between the electrodes 17a, 17b and the generator 52. As energy is supplied from the generator 52 and using the electrodes 17a, 17b to the grasped tissue, the light output of the visual indicator 60 receives current and begins to illuminate. Upon initial application of energy, impedance of the unsealed tissue is low, resulting in a lower illumination level by the light output of the indicator 60 because a lower amount of current will pass therethrough (favoring instead the electrical path with less impedance through the grasped tissue). As more energy is applied and tissue is sealed, impedance of the grasped tissue will increase, resulting in a higher illumination level by the light output because current through the visual indicator 60 will increase (resisting the electrical path through the grasped tissue). Illumination of the indicator 60 thus changes based on energy being applied, how much energy is applied, and tissue impedance to visually communicate the various indications provided above. The light output of the visual indicator 60 is illustrated as a light-emitting capacitor in FIG. 8, as well as in FIGS. 9-11, however various light sources can be used for the visual indicator 60, and the visual indicator 60 can also include a dielectric.

Figure 9:
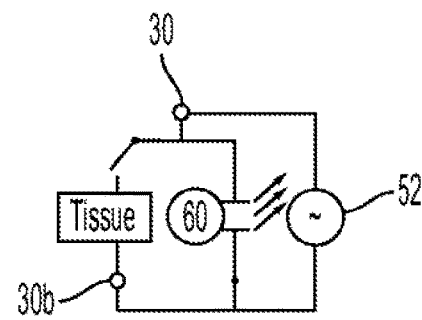
FIG. 9 is an electrical diagram of another embodiment of an electrical pathway for the surgical device of FIG. 1.

FIG. 9 illustrates one embodiment of a passive monopolar electrical configuration that communicates similar information as the electrical configuration in FIG. 8. The visual indicator 60, the energy source (such as the generator 52), and tissue contacted by the monopolar electrode 30 are connected in parallel with each other. In such an example, the tissue is also connected to a separate electrical return path, ground, or electrode 30b. Thus, contact between the monopolar electrode 30 and tissue adjacent the end effector 14 completes an electrical circuit when the tissue is also engaged with the electrical return path. This electrical configuration operates on tissue similarly to the bipolar configuration above in FIG. 8, as it allows the visual indicator 60 to indicate when energy is being applied by the electrode 30, an amount of energy being applied, various impedance levels to indicate whether tissue and/or a vessel contacted by the monopolar electrode 30 has been almost or is entirely sealed, etc.

In one exemplary embodiment, the device 100 includes the bipolar electrical configuration of FIG. 8 for use when the device 100 is in the bipolar mode and includes the passive monopolar electrical configuration of FIG. 9 for use when the device 100 is in the monopolar mode.

Figure 10:
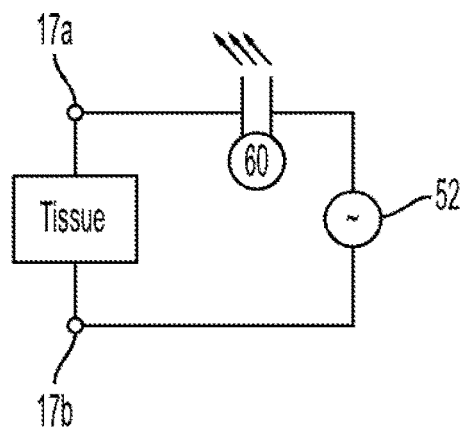
FIG. 10 is an electrical diagram of another embodiment of an electrical pathway for the surgical device of FIG. 1.

FIG. 10 illustrates another embodiment of a passive bipolar electrical configuration of the device 100. The visual indicator 60, the generator 52, and tissue contacted by the bipolar electrodes 17a, 17b are connected in series with each other. The indicator 60 in the electrical configuration of FIG. 10 indicates similar information and operates similarly to the indicator 60 in the electrical configuration of FIG. 8. When the indicator 60 and the electrodes 17a, 17b are arranged in series, as in FIG. 10, the light output of the visual indicator 60 initially has a higher illumination level when tissue impedance is lowest upon first tissue contact and treatment by the generator 52 through the electrodes 17a, 17b, opposite to the parallel configuration of FIGS. 8 and 9. Because tissue impedance is low initially, current will initially flow freely through the grasped tissue (and thus through the indicator 60). The illumination level is thus initially high and decreases during application of energy as tissue impedance rises and tissue and/or a vessel is sealed, resulting in greater resistance to current flow through the grasped tissue (and thus through the indicator 60).

Figure 11:
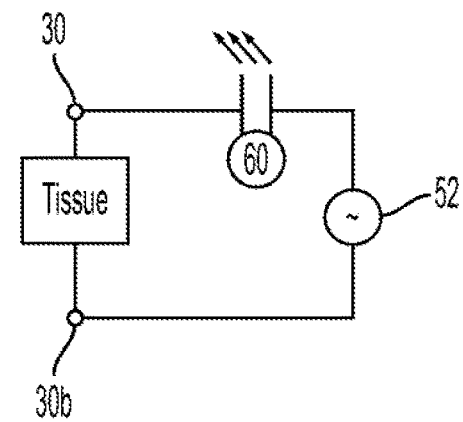
FIG. 11 is an electrical diagram of another embodiment of an electrical pathway for the surgical device of FIG. 1.

FIG. 11 illustrates another embodiment of a passive monopolar electrical configuration. The visual indicator 60, the generator 52, and tissue contacted by the monopolar electrode 30 are connected in series with each other. As with the monopolar configuration in FIG. 9, the tissue is also connected to a separate electrical return path, ground, or electrode 30b such that a complete electrical circuit is formed when the electrode 30 contacts tissue that is also in contact with the return path. Similar to the electrical configuration of FIG. 10, illumination of the indicator 60 is initially higher when tissue impedance is lowest upon first tissue contact and treatment. The illumination level will decrease during application of energy as tissue impedance rises and the contacted tissue and/or vessel is sealed.

In one exemplary embodiment, the device 100 includes the bipolar electrical configuration of FIG. 10 for use when the device 100 is in the bipolar mode and includes the passive monopolar electrical configuration of FIG. 11 for use when the device 100 is in the monopolar mode. In another exemplary embodiment, the device 100 includes the bipolar electrical configuration of FIG. 8 for use when the device 100 is in the bipolar mode and includes the passive monopolar electrical configuration of FIG. 11 for use when the device 100 is in the monopolar mode. In yet another exemplary embodiment, the device 100 includes the bipolar electrical configuration of FIG. 10 for use when the device 100 is in the bipolar mode and includes the passive monopolar electrical configuration of FIG. 9 for use when the device 100 is in the monopolar mode.

Figure 12:
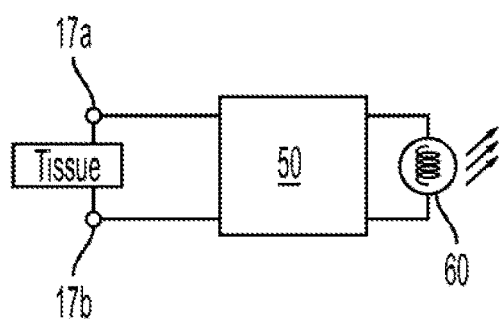
FIG. 12 is an electrical diagram of another embodiment of an electrical pathway for the surgical device of FIG. 1.

FIG. 12 illustrates another embodiment of a bipolar electrical configuration. However, the visual indicator 60 in FIG. 12 is active rather than passive and is thus configured to indicate information independently of when energy is being applied by the generator 52 to the bipolar electrodes 17a, 17b. The energy applied is sub-therapeutic to avoid unintentionally affecting tissue during active sensing and indicating. This permits the visual indicator 60 to actively communicate information before, during, and after tissue treatment, thus allowing a user to more accurately analyze a treatment situation without having to repeatedly apply energy to tissue. As such, illumination of the visual indicator 60 can indicate any tissue contact by the electrodes 17a, 17b, a tissue type of the contacted tissue through use of various tissue-sensing algorithm (such as algorithms discussed in U.S. patent application Ser. No. 16/115,247 entitled "Estimating The State Of The Jaw," which is incorporated by reference herein in its entirety, impedance levels of contacted tissue, etc. In such examples, the indicator 60 can also be used to alert a user if the wrong tissue type has been contacted, such an indicating when a ureter is contacted that the user should not treat.

Thus, FIG. 12 illustrates an active parallel bipolar configuration in which the visual indicator 60 in the form of a light source, a sub-therapeutic low-voltage AC signal (for example, as provided by the power source 50 or the generator 52), and tissue gripped by bipolar electrodes 17a, 17b are connected in parallel with each other. When tissue is grasped by the electrodes 17a, 17b, a complete electrical circuit is formed to allow current to flow therethrough. The current flow and impedance of tissue can be used to determine various information to be communicated by the indicator 60. For example, if tissue is grasped at all by the electrodes 17a, 17b, the indicator 60 can be configured to illuminate when current flows through the circuit upon completing the circuit. Depending on impedance of any grasped tissue, more or less current will flow through the indicator 60, and the level of current flowing therethrough can be used to determine impedance levels and/or a tissue type based on expected or pre-determined impedance levels of various tissue. The AC signals can be controlled or monitored by the processor 54 and/or one or more control circuits in the power source(s). The AC signals can be applied to the circuit at various selectable times, such as upon turning on the device, by actuating one or more buttons, switches, etc. that are selectively actuatable by the user, when various device modes are entered on the device housing 10, etc.

Figure 13:
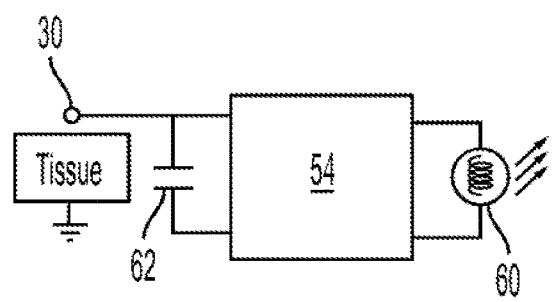
FIG. 13 is an electrical diagram of another embodiment of an electrical pathway for the surgical device of FIG. 1.

FIG. 13 illustrates another embodiment of a monopolar electrical configuration. FIG. 13 is similar to FIG. 12 in that its electrical configuration allows for active indication. The configuration of FIG. 13 can be used to indicate when tissue has been contacted by the end effector 14 (and more specifically, by the electrode 30 in the end effector 14). The configuration is a parallel monopolar electrical configuration in which the visual indicator 60, a capacitor 62 with a known capacitance, control circuitry that can measure voltage (for example, the processor 54, control circuitry in the power source 50, control circuitry in the generator 52, etc.), and tissue contacted by the monopolar electrode 30 are connected in parallel with each other. In such an electrical configuration, tissue also contacts some grounding source or return electrical path, as discussed above regarding other monopolar electrical configurations, to complete the electrical circuit when the monopolar electrode 30 comes into contact with tissue. As such, when tissue is contacted by the monopolar electrode 30, capacitance of the electrical configuration changes as a complete circuit is formed, causing current to flow through the electrical configuration and the indicator 60 to indicate that tissue has been contacted by the electrode 30.

In one exemplary embodiment, the device 100 includes the bipolar electrical configuration of FIG. 12 for use when the device 100 is in the bipolar mode and includes the monopolar electrical configuration of FIG. 13 for use when the device 100 is in the monopolar mode. In another exemplary embodiment, the device 100 includes the bipolar electrical configuration of FIG. 8 or FIG. 10 for use when the device 100 is in the bipolar mode and includes the monopolar electrical configuration of FIG. 13 for use when the device 100 is in the monopolar mode. In yet another exemplary embodiment, the device 100 includes the bipolar electrical configuration of FIG. 12 for use when the device 100 is in the bipolar mode and includes the monopolar electrical configuration of FIG. 9 or FIG. 11 for use when the device 100 is in the monopolar mode.

The electrical configurations of FIGS. 8-13 illustrate the visual indicator 60 in electrical communication with either the bipolar electrodes 17a, 17b or the monopolar electrode 30 such that illumination of the visual indicator 60 relies on electrical contact between the bipolar electrodes 17a, 17b or the monopolar electrode 30 and tissue of a patient. However, the surgical device 100 can additionally or alternatively incorporate electrical configurations that do not rely on tissue contact to complete a circuit. For example, subtherapeutic AC signals can be used to indicate whether the device 100 is turned on, to provide a light source to the operating site, etc. by arranging a visual indicator 60 in a complete electrical circuit with a source of AC signals (for example, as provided by the power source 50 or the generator 52) and an actuator using one or more electrical paths 46 in the device 100. When the actuator is activated, the circuit can be complete and AC signals can flow through the indicator 60 to cause illumination. Various actuators can be used either solely for actuation of the indicator 60, such as by actuating a button, switch, toggle, etc. on the device 100, or as part of another operation of the device 100, such as when powering on the device 100, plugging the device 100 into the generator 52, actuating one or more of the closure handle 20, the actuator 24, the actuator 26, etc.

In at least some embodiments, one or more electrical configurations can be incorporated into the device 100 such that the visual indicator 60 can communicate information based on sensor information from the device's sensor(s) rather than or in addition to interaction between the electrodes 17a, 17b, 30 and tissue and/or any independent illumination of an indicator by actuators. Various signal pathways can be formed by one or more electrical paths 46 between the indicator 60, the processor 54, and one or more sensors, such as sensors 18, 25. As such, the processor 54 can be configured to control an amount of current flowing through the indicator 60 to change illumination levels based on sensor readings. For example, rather than or in addition to having indicator illumination levels vary to indicate an amount of energy being applied to tissue as a direct result of applying more or less energy by having the indicator 60 electrically wired into the energy application circuitry (as shown in FIGS. 8-11 above), the processor 54, power source 50, and/or generator 52 can monitor energy levels being applied and provide one or more visual indicators 60 more or less current to increase or decrease illumination levels to indicate the amount of energy being applied. Such sensor readings can thus be used to convey similar information to that discussed above, such as tissue impedance values, whether the device 100 is turned on or off, tissue contact, tissue type, completed sealing of tissue and/or a vessel, etc., and they can also convey additional information that may be simpler to convey using sensor readings, such as whether the device 100 is in the monopolar mode or bipolar mode. The device 100 can include one or more visual indicators 60 that are passive and/or active, directly engaged in the electrode treatment circuitry and/or activated based on sensor data, and disposed on a variety of areas on the device to allow information about the device 100 to be presented to a user in multiple ways depending on a desired use of the device.

As mentioned above, the indicator 60 in the illustrated embodiment of FIGS. 1-7 is wrapped around the shaft 12 and extends into the lower jaw 16b. FIGS. 14-17 illustrate various other locations where one or more indicators can be located on a surgical device that is otherwise configured and used similar to that discussed herein form the device 100 of FIGS. 1-7. While specific locations of the visual indicators 60 are provided in device 100, visual indicators can be placed on a variety of different locations on surgical devices.

Figure 14:
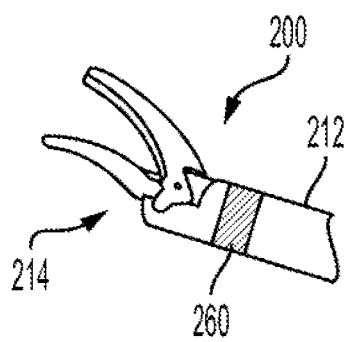
FIG. 14 is a perspective view of a distal portion of another embodiment of a surgical device.

FIG. 14 illustrates a device 200 including an end effector 214, a shaft 212, and a visual indicator 260 similar to visual indicator 60 that is disposed around a distal portion of the shaft 212. Unlike the indicator 60 of the device 100, the indicator 260 does not extend into any portion of the end effector 214.

Figure 15:
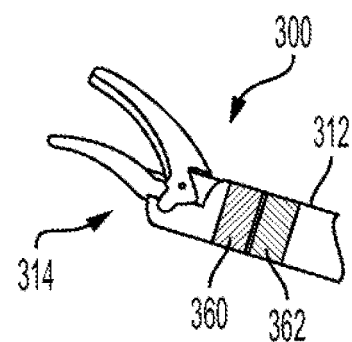
FIG. 15 is a perspective view of a distal portion of another embodiment of a surgical device.

FIG. 15 illustrates a surgical device 300 including an end effector 314, a shaft 312, and two visual indicators 360, 362 each disposed around a distal portion of the shaft 312. In an exemplary embodiment, the indicators 360, 362 are configured to show different information from one another. As one example, the indicators 360, 362 can be configured to illuminate in different colors from one another. The indicator 360 can be configured to illuminate in one color, e.g. yellow, when the device 300 is in a bipolar mode, and the indicator 362 can be configured to illuminate in another color, e.g. blue, when the device 300 is in a monopolar mode. Thus, only one of the indicators 360, 362 can be illuminated at a time since a device cannot be simultaneously in both bipolar mode and monopolar mode. For another example, the indicators 360, 362 can be configured to indicate various information independently from each other such that both indicators 360, 362 may be illuminated at the same time, such as energy being applied or not for the indicator 360 and the device 300 being on or off for the indicator 362.

Figure 16:
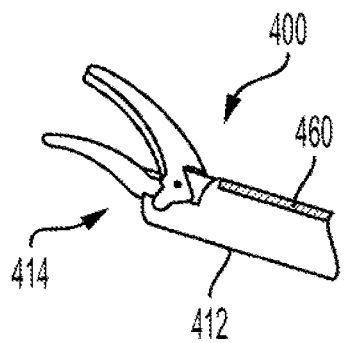
FIG. 16 is a perspective view of a distal portion of another embodiment of a surgical device.
Figure 17:
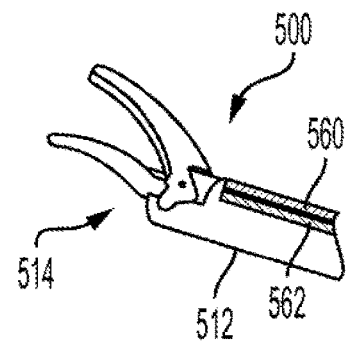
FIG. 17 is a perspective view of a distal portion of another embodiment of a surgical device.

The indicators 60, 260, 360, 362 of FIGS. 1-7, 14, and 15 extend radially around their respective shafts 12, 212, 312. One or more indicators can extend longitudinally along the shaft of a device and/or longitudinally along a handle. For example, FIG. 16 illustrates a surgical device 400 including an end effector 414, a shaft 412, and a visual indicator 460 extending longitudinally along at least a distal portion of the shaft 412. For another example, FIG. 17 illustrates a surgical device 500 including an end effector 514, a shaft 512, and two visual indicators 560, 562 extending longitudinally along at least a distal portion of the shaft 512. The indicators 460, 560, 562 do not extend into their respective end effectors 414, 514 but could do so in other embodiments.

Figure 18:
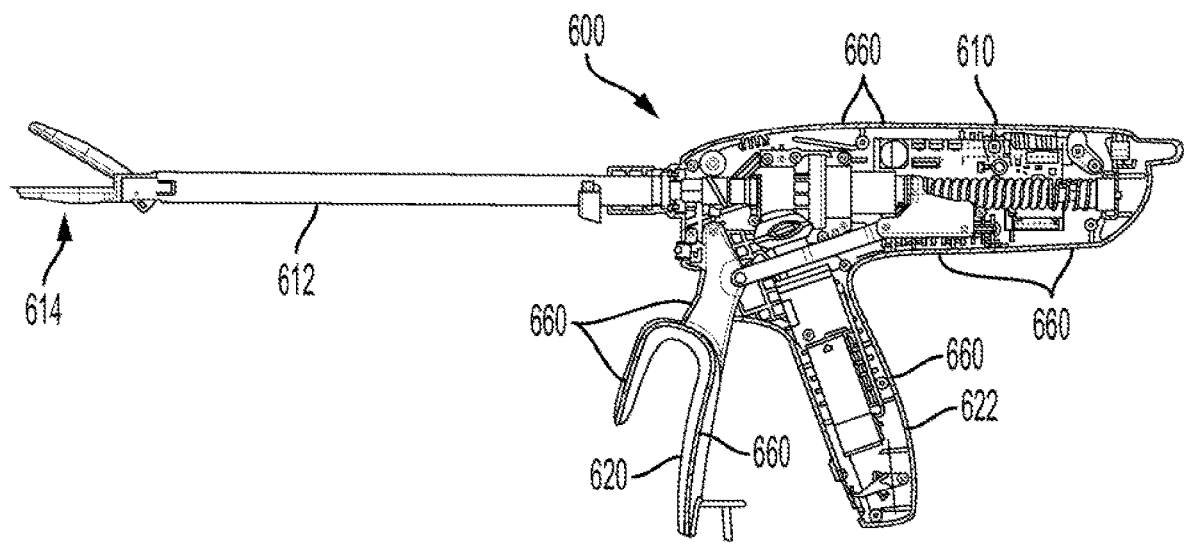
FIG. 18 is a cross-sectional side schematic view of another embodiment of a surgical device.

Instead of or in addition to an indicator being at a shaft and/or end effector of a surgical device, an indicator can be at the device's housing. FIG. 18 illustrates a device 600 including an end effector 614, a shaft 612, a housing 610 including a stationary grip handle 622, a closure grip handle 620, and a visual indicator 660. The indicator 660 is disposed along external edges of the housing 610 but can be placed along any edges or surfaces of the housing 610 visible from outside the housing.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrosurgical device, comprising:
   a housing;
   an elongate shaft extending from the housing;
   an end effector operatively connected to a distal end of the elongate shaft, the end effector including first and second jaws movable between an open position, in which the first and second jaws are spaced apart from one another, and a closed position, in which the first and second jaws cooperate to grasp tissue therebetween, the end effector including an electrode configured to conduct radio frequency (RF) energy to the tissue in contact therewith;
   an electro-luminescent (EL) material wrapped around an external surface of the elongate shaft and extending into the second jaw, the EL material configured to provide a light output indicative of a status of the electrosurgical device; and
   a sensor in the end effector configured to measure impedance of the tissue contacted by the electrode;
   wherein the external surface of the elongate shaft is a conductive material;
   the EL material includes a dielectric coating above and in contact with the conductive material;
   the EL material includes a phosphor coating above and in contact with the dielectric coating; and
   the EL material includes a conductive transparent layer above and in contact with the phosphor coating.

2. The electrosurgical device of claim 1, wherein the EL material is configured to provide the status that includes whether the tissue contacted by the electrode has been sealed by the energy conducted thereto such that a low measured impedance indicates that the tissue is unsealed and a high measured impedance indicates that the tissue is sealed.

3. The electrosurgical device of claim 1, wherein the light output is configured to be at least one of turned on and off, rhythmically pulse, or illuminate in one or more pre-set colors.

4. The electrosurgical device of claim 1, wherein the EL material is configured to provide the status of the electrosurgical device that includes at least one of an energy modality of the electrosurgical device between monopolar and bipolar modes, if the electrosurgical device is turned on or off, if the RF energy is being presently applied by the electrode to the tissue in contact therewith, an amount of the RF energy being presently applied, if an error occurred during RF energy application, if the electrode has contacted the tissue, or a type of the tissue that the electrode has contacted.

5. The electrosurgical device of claim 1, wherein the electrode includes at least one of a monopolar electrode or a bipolar electrode assembly including an active electrode and a return electrode.

6. The electrosurgical device of claim 1, wherein the EL material is configured to receive energy from at least one of the RF energy of the end effector or a sub-therapeutic electrical signal in the electrosurgical device.

7. The electrosurgical device of claim 1, further comprising an actuator configured to control the EL material.

8. The electrosurgical device of claim 1, wherein the EL material is configured to be controlled by at least one of an amount of the RF energy applied to the end effector or a sound in an operating room environment in which the electrosurgical device is used.

9. The electrosurgical device of claim 1, wherein the phosphor coating is configured to glow when exposed to alternating current of the RF energy.

10. An electrosurgical device, comprising:
    a housing;
    an elongate shaft extending from the housing;
    an end effector coupled to a distal end of the elongate shaft, the end effector being configured to deliver energy to tissue in contact with the end effector, the end effector having a cutting element configured to extend at least partially therethrough to transect the tissue grasped by the end effector; and
    an electro-luminescent (EL) light assembly sprayed or painted on the cutting element of the end effector, the EL light assembly being configured to display variable real-time information about at least one of an operation of the end effector or a condition of the tissue in contact with the end effector.

11. The electrosurgical device of claim 10, wherein the EL light wherein the EL material is configured to provide the status that includes assembly is configured to be at least one of turned on and off, rhythmically pulse, or illuminate in one or more pre-set colors.

12. The electrosurgical device of claim 10, wherein the EL light assembly is configured to be electrically connected in parallel with the tissue in contact with the end effector such that a brightness of the EL light assembly increases as the energy is applied to seal the tissue.

13. The electrosurgical device of claim 10, the EL light assembly is configured to be electrically connected in series with the tissue in contact with the end effector such that a brightness of the EL light assembly decreases as the energy is applied to the tissue.

14. The electrosurgical device of claim 10, further comprising an actuator configured to be actuated and thereby cause the cutting element to advance relative to the end effector so as to transect the tissue grasped by the end effector;
    wherein the EL light assembly is configured to display variable real-time information about at least the operation of the end effector, the operation of the end effector including the actuation of the actuator.

15. A surgical method, comprising:
    positioning an end effector of an electrosurgical device in contact with tissue, the end effector being coupled to a distal end of an elongate shaft of the surgical device; and
    actuating the electrosurgical device to deliver energy to the tissue with an electro-luminescent (EL) light assembly, which is wrapped around an external surface of the elongate shaft of the electrosurgical device and extends into the end effector, displaying variable real-time information about at least one of an actuation state of the electrosurgical device or a condition of the tissue in contact with the end effector;

wherein actuating the electrosurgical device to deliver the energy to the tissue includes delivering the energy to seal the tissue until the EL light assembly indicates that the tissue is sealed;

wherein the EL light assembly indicating the tissue is sealed further includes the end effector measuring impedance of the tissue such that a low measured impedance indicates that the tissue is unsealed and a high measured impedance indicates that the tissue is sealed; and wherein the EL light assembly extends into a jaw of the end effector and extends longitudinally along the jaw such that the EL light assembly is visible with the end effector in an open position and is not visible with the end effector in a closed position.

16. The method of claim 15, wherein the EL light assembly is configured to be at least one of turned on and off, rhythmically pulse, or illuminate in one or more pre-set colors.

17. A surgical method, comprising:
positioning the end effector of the electrosurgical device of claim 1 in contact with the tissue; and
actuating the electrosurgical device to deliver the RF energy to the tissue with the EL light material providing the light output and thereby displaying variable real-time information about the status of the electrosurgical device, the status of the electrosurgical device being at least one of an actuation state of the electrosurgical device or a condition of the tissue in contact with the end effector.

18. The method of claim 17, wherein actuating the electrosurgical device to deliver the RF energy to the tissue includes delivering the RF energy to seal the tissue until the EL light assembly indicates that the tissue is sealed.

19. A surgical method, comprising:
positioning an end effector of an electrosurgical device in contact with tissue, the end effector being coupled to a distal end of an elongate shaft of the surgical device: and
actuating the electrosurgical device to deliver energy to the tissue with an electro-luminescent (EL) light assembly, which is wrapped around an external surface of the elongate shall of the electrosurgical device and extends into the end effector, displaying variable real-time information about at least one of an actuation state of the electrosurgical device or a condition of the tissue in contact with the end effector;

wherein actuating the electrosurgical device to deliver the energy to the tissue includes delivering the energy to seal the tissue until the EL light assembly indicates that the tissue is sealed;

the EL light assembly indicating the tissue is sealed further includes the end effector measuring impedance of the tissue such that a low measured impedance indicates that the tissue is unsealed and a high measured impedance indicates that the tissue is sealed;

the external surface of the elongate shaft is a conductive material;

the EL material includes a dielectric coating above and in contact with the conductive material;

the EL material includes a phosphor coating above and in contact with the dielectric coating; and the EL material includes a conductive transparent layer above and in contact with the phosphor coating.

20. The method of claim 19, wherein the EL light assembly is configured to be at least one of turned on and off, rhythmically pulse, or illuminate in one or more pre-set colors.

* * * * *